United States Patent

Laurent et al.

[11] Patent Number: 4,673,673
[45] Date of Patent: Jun. 16, 1987

[54] 17α-ALKYL-17β-HYDROXY-1α-METHYL-4-ANDROSTEN-3-ONES, THEIR PRODUCTION AND USE PHARMACEUTICALLY

[75] Inventors: Henry Laurent; Rudolf Wiechert, both of Berlin, Fed. Rep. of Germany

[73] Assignee: Schering Aktiengesellschaft, Berlin and Bergkamen, Fed. Rep. of Germany

[21] Appl. No.: 762,894

[22] Filed: Aug. 6, 1985

Related U.S. Application Data

[63] Continuation of Ser. No. 661,290, Oct. 17, 1984, abandoned, which is a continuation of Ser. No. 531,785, Sep. 13, 1983, abandoned, which is a continuation of Ser. No. 367,865, Apr. 13, 1982, abandoned.

[30] Foreign Application Priority Data

Apr. 13, 1981 [DE] Fed. Rep. of Germany ....... 3115996

[51] Int. Cl.$^4$ .......................... A61K 31/56; C07J 9/00
[52] U.S. Cl. ................................. 514/178; 260/397.4
[58] Field of Search ...................... 260/397.4; 514/178

[56] References Cited

U.S. PATENT DOCUMENTS 3,391,168  7/1968  Counsell et al. ................ 260/397.4
3,705,180 12/1972  Klimstra ........................... 260/397.4
4,344,941  9/1982  Wiechert et al. ................ 260/397.4

OTHER PUBLICATIONS

Chemical Abstracts vol. 76, (1972), Par. 154025T.

Primary Examiner—Leonard Schenkman
Assistant Examiner—Joseph A. Lipovsky
Attorney, Agent, or Firm—Millen & White

[57] ABSTRACT

17α-Alkyl-17β-hydroxy-1α-methyl-4-androsten-3-ones of the formula

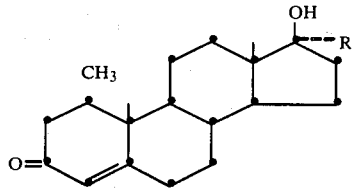

wherein R is a straight-chain alkyl residue of 3-8 carbon atoms, i.e., $C_{3-8}$-n-alkyl, are pharmacologically active compounds distinguished by antiandrogenic activity, especially upon topical application.

6 Claims, No Drawings

17α-ALKYL-17β-HYDROXY-1α-METHYL-4-ANDROSTEN-3-ONES, THEIR PRODUCTION AND USE PHARMACEUTICALLY

This is a continuation of application Ser. No. 661,290, filed Oct. 17, 1984, which is a continuation of Ser. No. 531,785, filed Sept. 13, 1983, which is a continuation of Ser. No. 367,865, filed Apr. 13, 1982, all of which are abandoned.

BACKGROUND OF THE INVENTION

The present invention relates to 17α-alkyl-17β-hydroxy-1α-methyl-4-androsten-3-ones having highly desirable topical antiandrogenic activity.

17β-Hydroxy-1α,17α-dimethyl-4-androsten-3-one has been known for a long time. It is distinguished inter alia by an anabolic activity [F. Neumann and R. Wiechert, Arzneimittelforschung [Drug Research] 15: 1968 et seq., specifically 1177 (1965)].

SUMMARY OF THE INVENTION

It is an object of this invention to provide novel compounds having advantageous pharmacological activity.

Upon further study of the specification and appended claims, further objects and advantages of this invention will become apparent to those skilled in the art.

These objects have been attained by providing 17α-alkyl-17β-hydroxy-1α-methyl-4-androsten-3-ones of Formula I

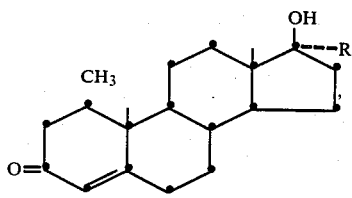

wherein R is a straight-chain alkyl residue of 3-8 carbon atoms, i.e., $C_{3-8}$-n-alkyl, which are pharmacologically active compounds distinguished by antiandrogenic activity, especially upon topical application.

DETAILED DISCUSSION

The 17α-alkyl-17β-hydroxy-1α-methyl-4-androsten-3-ones of Formula I are, surprisingly, distinguished by a pronounced antiandrogenic effectiveness when applied locally. Upon systemic administration, these compounds do not exhibit a marked antiandrogenic activity. This dissociation of activity between these two modes of administration distinguishes them advantageously over all known commercial preparations of the same type of activity. Moreover, the compounds of this invention have the advantage that they strongly inhibit lipogenesis.

The antiandrogenic activity can be determined by conventional protocols. For example, the following method can be used.

Male, fertile hamsters weighing about 80 g are castrated and subcutaneously substituted daily with 0.1 mg of testosterone propionate. Twice daily, the right ear is treated with 0.01 ml of a 3% solution of the test compound in acetone or ethanol for a period of three weeks. In the control group, the right ear is treated merely with 0.01 ml of solvent.

On the 22nd day, the animals are sacrificed with ether; the seminal vesicle is prepared and weighed. Respectively defined tissue areas having an edge length of 3×7 mm are punched out from the ears. These are further treated histologically, and the areas of the sebaceous glands are measured. By comparing the areas of the ventral side of the ears of the animals treated with the antiandrogen with the same regions in the animals treated merely with solvent, a measure is obtained of the local antiandrogenic effect of the test compound. The reduction in weight of the seminal vesicle observed in comparison with a control group demonstrates the extent of the systemic antiandrogenic activity of the test compound.

The effect of the test compounds on lipogenesis can be determined by conventional protocols, e.g., as follows:

Male, fertile hamsters weighing 80–100 g are castrated and daily substituted subcutaneously with 0.1 mg of testosterone propionate. The right ear of each test animal is treated twice daily with 0.01 ml of a 1% solution of the test compound in acetone (in case of the control group, each is treated only with 0.01 ml of solvent) for a period of three weeks. The animals are then sacrificed. A defined tissue area of a diameter of 8 mm is punched out from the treated right ear of each, as well as from the untreated left ear.

The ventral and dorsal sides of the punched-out sections are separated from each other along the ear cartilage. They are immediately transferred into Dulbecco's modification of Eagle's medium, to which had been added 4 millimoles of glutamine and 10% calf serum, and to avoid microbial contamination, which also contained 100 IU/ml of penicillin, 100 μg/ml of streptomycin, 125 μg/ml of kanamycin, 25 IU/ml of nystatin, and 10 μg/ml of gentamycin. They are incubated at 37° C. for one hour.

Thereafter, the punched-out sections are introduced under aseptic conditions into fresh culture medium containing 1 μCi/ml of $C^{14}$-labeled sodium acetate, and incubated at 37° C. for 4 hours. The specimens are then introduced into 2 ml of a proteolysis solution made up of 0.05 mole of tris buffer having a pH of 7.5, 0.01 mole of disodium ethylenediaminetetraacetic acid, 0.5% of sodium dodecyl sulfate, and 0.1% of proteinase K (E. Merck A. G., Darmstadt, Federal Republic of Germany). The mixture is incubated for 24 hours at 37° C.

The thus-obtained specimens are extracted once with 5 ml of chloroform and once more with 3 ml of chloroform, the combined chloroform extracts are concentrated under vacuum, and the content of radiolabeled lipids in the extracts is determined by a scintillation counter. The percent inhibition of the lipogenesis of the treated group is calculated by comparison with the control group treated solely with solvent.

The following table shows the results obtained in these tests.

TABLE

| No. | Compound | Areal Reduction of Sebaceous Glands | | Weight Reduction of Seminal Vesicle | Change in Lipogenesis | |
|---|---|---|---|---|---|---|
| | | Treated Ear | Contralateral Ear | | Treated Ear | Contralateral Ear |
| 1 | 17β-Hydroxy-1α-methyl-17α-propyl-4-androsten-3-one | 68% | 46% | 0% | −45% | −31% |
| 2 | 17α-Butyl-17β-hydroxy-1α-methyl-4-androsten-3-one | 64% | 34% | 0% | −48% | −26% |

For topical application, the compounds of this invention can be processed together with the conventional excipients into solutions, gels, ointments, powders, or other preparations. Suitable excipients include, for example, water, ethanol, propanol, glycerin, methylcellulose, hydroxypropylcellulose, carboxypolymethylene, etc. The antiandrogen of this invention is preferably utilized in a concentration of 0.05-5.0% by weight, based on the total weight of the preparation. The preparations can be utilized for the topical treatment of diseases such as acne, seborrhea, alopecia, and hirsutism. They can be administered analogously to the known agent cyproterone acetate.

The novel 17α-alkyl-17β-hydroxy-1α-methyl-4-androsten-3-ones of this invention can be produced by a process comprising reacting a compound of Formula II

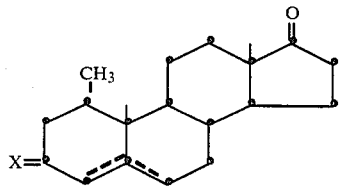

(II)

wherein
one of the bonds - - - - represents a double bond, and
X is an oxo group, an oximino group, an alkoxy group of 1-4 carbon atoms and a hydrogen atom, or an alkylenedioxy group of 2-6 carbon atoms, with an organo-metal compound of Formula III

RZ  (III)

wherein
R is as defined above and
Z is an alkali metal ion (e.g., lithium) or a magnesium halide ion.

This process can be conducted under conditions well-known to those skilled in the art [H. Laurent and R. Wiechert in: John Fried and John A. Edwards "Organic Reactions in Steroid Chemistry" II: 52 et seq. (1972) van Nostrand Reinhold Company, New York, etc., whose disclosure is incorporated by reference herein].

All of the compounds of Formula II are either known or readily preparable from known compounds using fully conventional procedures such as those exemplified below.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

(A) A solution of 7.0 g of 17β-hydroxy-1α-methyl-4-androsten-3-one in 500 ml of benzene is combined with 80 ml of 1,2-ethanediol and 400 mg of p-toluenesulfonic acid and the evolving water is distilled off azeotropically within 20 hours. After cooling of the reaction mixture, the latter is combined with 5 ml of pyridine, washed with water, dried over sodium sulfate, and concentrated under vacuum. The residue is chromatographed on silica gel, thus obtaining with hexane-ethyl acetate gradients (25-30% ethyl acetate) 6.3 g of 3,3-ethylenedioxy-1α-methyl-5-androsten-17β-ol.

(B) 3.6 g of 3,3-ethylenedioxy-1α-methyl-5-androsten-17β-ol is dissolved in 100 ml of dichloromethane, combined with 5.8 g of pyridinium dichromate, and agitated for 20 hours at room temperature. The reaction solution is washed with water, dried, and evaporated under vacuum. The residue is chromatographed on silica gel, thus obtaining with hexane-ethyl acetate gradients (11-16% ethyl acetate) 2.81 g of 3,3-ethylenedioxy-1α-methyl-5-androsten-17-one.

(C) Under agitation, a 1.7-molar solution of propyllithium in diethyl ether is added dropwise at −70° C. to a solution of 2.27 g of 3,3-ethylenedioxy-1α-methyl-5-androsten-17-one in 80 ml of tetrahydrofuran. After 30 minutes, the reaction mixture is poured into ice water, extracted with diethyl ether, washed with water, and the organic phase is dried over sodium sulfate and evaporated to dryness under vacuum, thus obtaining 2.40 g of 3,3-ethylenedioxy-1α-methyl-17α-propyl-5-androsten-17β-ol.

(D) 2.40 g of 3,3-ethylenedioxy-1α-methyl-17α-propyl-5-androsten-17β-ol is dissolved in 70 ml of acetone. The solution is combined with 5 ml of water and 460 mg of pyrridinium p-toluenesulfonate, heated to boiling for 3 hours, and then concentrated under vacuum. The residue is dissolved in 300 ml of ethyl acetate, the solution is washed with water, dried over sodium sulfate, and concentrated under vacuum. The crude product is chromatographed on silica gel, thus obtaining with hexane-acetone gradients (10-12% acetone), after recrystallization from diethyl ether-petroleum ether, 724 mg of 17β-hydroxy-1α-methyl-17α-propyl-4-androsten-3-one, mp 88° C.

EXAMPLE 2

(A) Under argon, 5 ml of a 1.2-molar solution of butyllithium in hexane is added dropwise at −70° C. to a solution of 1.27 g of 3,3-ethylenedioxy-1α-methyl-5-androsten-17-one in 50 ml of tetrahydrofuran. After 15 minutes, the reaction mixture is poured into ice water, extracted with diethyl ether, the organic phase washed with water, dried over sodium sulfate, and concentrated under vacuum, thus obtaining 1.30 g of 17α-butyl-3,3-ethylenedioxy-1α-methyl-5-androsten-17β-ol as a crude product.

(B) A solution of 1.30 g of 17α-butyl-3,3-ethylenedioxy-1α-methyl-5-androsten-17β-ol in 40 ml of acetone is combined with 3 ml of water and 250 mg of pyridinium p-toluenesulfonate and heated to boiling for 3 hours. The reaction mixture is worked up as described in Example 1(D), the resultant crude product is chromatographed on silica gel with hexane-ethyl acetate gradients (16–18% ethyl acetate), and recrystallization from diethyl ether-petroleum ether yields 696 mg of 17α-butyl-17β-hydroxy-1α-methyl-4-androsten-3-one, mp 85° C.

EXAMPLE 3

(A) A solution of 10.0 g of 3,3-ethylenedioxy-1α-methyl-5-androsten-17-one in 100 ml of diethyl ether is combined under argon at −30° C. within 30 minutes dropwise with 40 ml of a 1.5-molar solution of hexyllithium in diethyl ether. The reaction mixture is then stirred for one hour at −30° C. and subsequently poured into ice water, extracted with diethyl ether, the organic phase washed with water, dried over sodium sulfate, and concentrated under vacuum. The residue is chromatographed on silica gel, thus obtaining with hexane-ethyl acetate gradients (15–25% ethyl acetate) 5.36 g of 3,3-ethylenedioxy-17α-hexyl-1α-methyl-5-androsten-17β-ol.

(B) 5.36 g of 3,3-ethylenedioxy-17α-hexyl-1α-methyl-5-androsten-17β-ol is combined with 60 ml of 90% acetic acid and heated for 15 minutes on a steam bath. After cooling, the solution is stirred into ice water, the precipitated product is filtered off, washed, and dried. The crude product is chromatographed on silica gel, thus obtaining with hexane-ethyl acetate gradients (20–25% ethyl acetate), after recrystallization from diethyl ether-diisopropyl ether, 3.47 g of 17α-hexyl-17β-hydroxy-1α-methyl-4-androsten-3-one, mp 84° C.

EXAMPLE 4

Under the conditions described in Example 3(A), 8.46 g of 3,3-ethylenedioxy-1α-methyl-5-androsten-17-one is reacted with 40 ml of a 1.4-molar solution of pentyllithium in diethyl ether, then worked up, and the product is 3,3-ethylenedioxy-1α-methyl-17α-pentyl-5-androsten-17β-ol. This compound is hydrolyzed with 90% acetic acid under the conditions of Example 3(B), then worked up, and the resultant product is 3.16 g of 17β-hydroxy-1α-methyl-17α-pentyl-4-androsten-3-one, mp 144° C.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 17α-alkyl-17β-hydroxy-1α-methyl-4-androsten-3-one of the formula

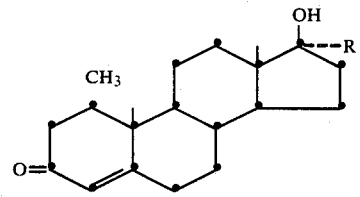

wherein R is n-alkyl of 7 or 8 carbon atoms.

2. A pharmaceutical composition comprising an antiandrogenically effective amount of a compound of claim 1 and a pharmaceutically acceptable carrier.

3. A pharmaceutical composition of claim 2 wherein the carrier is suitable for topical administration.

4. A pharmaceutical composition of claim 3 wherein the concentration of antiandrogenic compound is 0.5–5.0 wt. %.

5. A method of achieving an antiandrogenic effect in a patient in need of such treatment comprising topically administering to the patient an antiandrogenically effective amount of a compound of claim 1.

6. A method of claim 5 where the patient is suffering from acne, seborrhea, alopecia or hirsutism.

* * * * *